Dec. 3, 1935. R. L. BYRUM Plant Pat. 154
ROSE
Filed Jan. 9, 1935
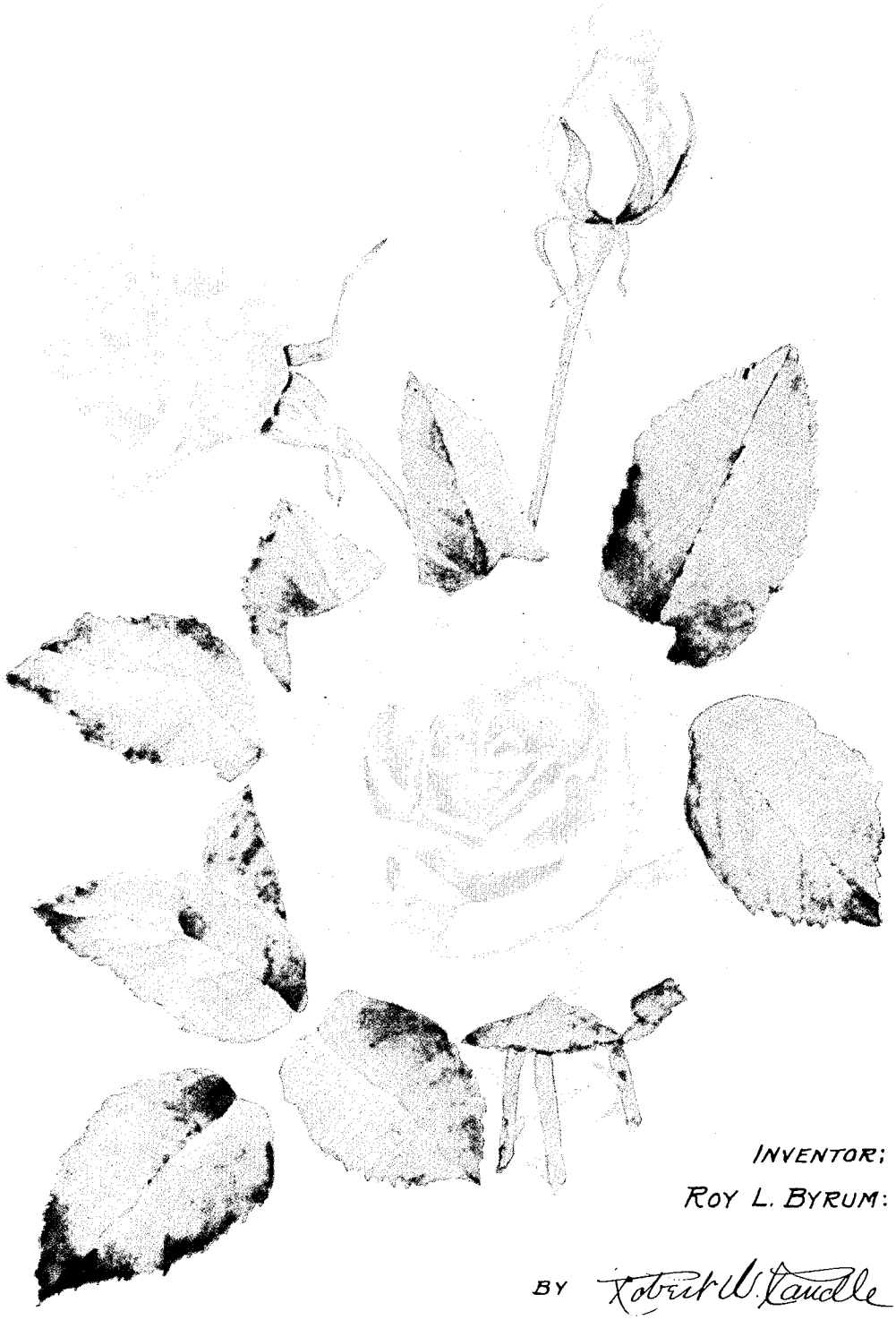
INVENTOR:
ROY L. BYRUM:
BY Robert W. Caudle
ATTORNEY.

Patented Dec. 3, 1935 Plant Pat. 154

UNITED STATES PATENT OFFICE

154

ROSE

Roy L. Byrum, Richmond, Ind., assignor to Joseph H. Hill Company, Richmond, Ind., a corporation of Indiana Application January 9, 1935, Serial No. 1,041

1 Claim. (Cl. 47—61)

The subject of this application for plant patent is classed as a hybrid tea-rose, and it is of the ever blooming type, it is a seedling of a "Sweet Adeline" rose, which is shown in Rose Patent No. 6; crossed with a "Joanna Hill" rose, which is registered but not patented.

*Generation.*—I produced this new rose by hybridization, employing a Sweet Adeline rose as the male parent and a Joanna Hill rose as the female parent. The combination of said two varieties of roses was attained as follows: In the month of March, of the year 1930, I collected pollen from the stamens of said male parent and deposited it on the stigmas which conducted it into the ovaries of the female parent. From the product of the above I obtained roses of three distinct new varieties, each of which presented certain new and distinct features, one of which is the subject of this application, and it is shown, as nearly as was possible, in the accompanying illustration, in three stages of development.

One of said roses, which is the subject of this application, was produced by hybridization, and close personal supervision, whereby the features, herein shown and described, became fixed as a new variety of roses, which features I will now describe as fully and as clearly as I may.

The discovery, development and completion of this rose as a new variety, was made in the greenhouses of the Joseph H. Hill Company, in Richmond, Indiana, and it is believed that its characteristics, as a new variety, became fixed and permanent in December, 1934, and immediately thereafter the following description was made from flowers grown in said greenhouses of the Joseph H. Hill Company.

*Buds.*—The buds of this rose are large and ovoid in shape and are of a bright apricot color, similar to that of "Afterglow" (Plant Patent No. 9), except as to the bright tinge which my rose presents. Usually each of the buds is inclosed by bright green sepals which extend upwardly from their globular receptacle.

*Flowers.*—The flowers are double, firm, full and graceful in appearance when they are fully opened. The flowers are usually four to six inches in diameter. There are twenty-five to thirty-five petals to each flower. When the flowers are first open the shape of the periphery thereof is slightly escalloped and tapering outwardly from their high center. The upper faces of the petals are velvety, and the under sides thereof are the same, except that they are slightly lighter in color.

The color of the bloom, taken as a whole and viewed as located at a distance therefrom, appears as of an apricot color, similar to but slightly lighter than that shown in Plant Patent No. 9, but when examined more closely it shows several shades of color, as follows: As it opens it changes to a creamy apricot color, with a slight touch of pink at the outer portion of the flower. The petals are rather thin and delicate in texture, and they retain their fully open shape and their colors for several days after the bloom becomes fully opened. Some specimens darken with age, having at maximum of beauty the inner portions of the petals dark apricot, outer faces light pink. Fully open bloom has central portion protruding outwardly in a graceful curve. Fragrance is moderate, tea, very delicate and pleasing.

The quantity of bloom to each bush is abundant.

The flowers bloom continuously throughout the year.

*Stamens.*—The stamens are numerous and of various lengths, with buff anthers. The filaments are white and are not prominent. Pollen is dark yellow, gradually becoming brown as it matures.

*Pistils.*—The pistils are numerous and of varying lengths, and are of a yellowish color, and the stigmas are white to light yellow.

*Foliage.*—The foliage is heavy and is composed of compound leaves of usually three leaflets nearest the flow and five to seven further down on the stems. The leaflets are usually oval and slightly elongated. The upper surface of the leaves are dark green and their lower sides are pale green, with the new growth much lighter.

The bush is of quick and vigorous growth, with many branches, and the stems are long, strong, and compact, erect and not inclined to bend. The body stalks are strong and of medium length.

What I claim, and desire to secure by Letters Patent, is:

The new variety of rose, herein shown and described, characterized by its continuity in blooming, the dark apricot color of the bloom, with the outer portion of the petals appearing as almost white with a pinkish tinge, shading into a creamy apricot color with a pinkish tinge toward the inner portion of the bloom when fully opened, with the inner portion of the petals merging into a dark apricot color at their maximum of development, and the attractiveness and beauty as an entirety.

ROY L. BYRUM.